United States Patent [19]
Hoffmann et al.

[11] Patent Number: 6,136,849
[45] Date of Patent: Oct. 24, 2000

[54] **ANTIBACTERIAL AND ANTIFUNGAL FLAVANONES FROM *EYSENHARDTIA TEXANA***

[76] Inventors: Joseph J. Hoffmann, 2718 E. Hendrick, Tuscon, Ariz. 85716; Gerald A. Wächter, 1311 W. Prince Rd., Tuscon, Ariz. 85705; Jordan U. Gutterman, 1707 Hermann Dr., Houston, Tex. 77004

[21] Appl. No.: 09/413,065

[22] Filed: Oct. 6, 1999

Related U.S. Application Data

[60] Provisional application No. 60/103,450, Oct. 6, 1998, abandoned.

[51] Int. Cl.[7] ............................ A61K 31/35; C07D 311/32
[52] U.S. Cl. ............................................ 514/456; 549/403
[58] Field of Search ............................. 549/403; 514/456

[56] References Cited

PUBLICATIONS

Harborne, The Flavonoids Advances in Research Since 1986, London: Chapman and Hall, p. 426, 1994.

Chem. Abstracts, vol. 61, Abstr. No. 9976h, Rashba, Mikrobiol. Zh., Akad. Nau, Ukr. RSR, vol. 26(2),p. 26–31 (1964).

Rozsa et al, Phytochemistry, vol. 23, No. 8, p. 1818 and 1819, 1984.

Rousis et al, Phytochemistry, vol. 26, No. 8, p. 237–2375, 1987.

Birch et al, Chem. Soc. Journal, p. 2063–2066, 1960.

Chem. Abstr,, vol. 128, No. 2, Abstr. No. 13147q, Jpn Kokai 09–301915, May 1996, 1998.

Iinuma et al, J. Pharm. Phamacology, vol. 46, p. 892–895, 1994.

*Primary Examiner*—Bernard Dentz
*Attorney, Agent, or Firm*—Benjamin Aaron Adler

[57] ABSTRACT

An activity-guided fractionation of a methanol-dichloromethane extract obtained from the aerial parts of *Eysenhardtia texana* Kunth. (Fabaceae) led to the isolation of two new antibacterial and antifungal flavanones. Their structures were established as 4',5,7-trihydroxy-8-methyl-6-(3-methyl-[2-butenyl])-(2S)-flavanone and 4',5,7-trihydroxy-6-methyl-8-(3-methyl-[2-butenyl])-(2S)-flavanone on the basis of their UV, ID and 2D-NMR spectra. These compounds have potent antibacterial and antifungal activity as measured by bioassay.

13 Claims, 1 Drawing Sheet

ANTIBACTERIAL AND ANTIFUNGAL FLAVANONES FROM *EYSENHARDTIA TEXANA*

CROSS-REFERENCE TO RELATED APPLICATIONS

This patent application claims benefit of priority of U.S. provisional application U.S. Ser. No. 60/103,450, filed Oct. 6, 1998, now abandoned.

BACKGROUND OF THE INVENTION

1. Field of the Invention

The present invention relates generally to the fields of organic chemistry, medical bacteriology and medical mycology. More specifically, the present invention relates to the identification of antibacterial and antifungal flavanones.

2. Description of the Related Art

Flavanoids, a wide-spread group of water-soluble phenolic derivatives in plants, are structurally based on the flavan moiety and consist of two aromatic rings joined in a chroman structure by a three carbon unit ($C_6$–$C_3$–$C_6$).

These phenylchroman ring systems include flavanones, flavones, flavanols, flavans, catechins and anthrocyanidins which are classified according to the state of oxidation of the $C_3$ unit; i.e., corresponding to carbons-2,3,4 in the molecule. The variety of compounds within the flavanoid group results from the hydroxylation of one, two or more of the carbon atoms in rings A and B, especially, carbons 2, 3 and 4 of the flavan structure. The hydroxyl groups may be further glycosylated, acylated, alkylated or isoprenylated.

Modern microbiological techniques have demonstrated that higher plants frequently exhibit significant potency against human bacterial and fungal pathogens and that the compounds isolated and/or subsequently synthesized possess therapeutic potential. A wide variety of flavanoids with prenyl substituents exhibit growth inhibitory activity against several microorganisms. Plants of the legume family (Leguminosae, Fabaceae) are known to produce a variety of bioactive compounds, among them antiinfective, antimicrobial or antibacterial flavanones.

The structure-activity relationship among flavanones indicates that a 2′, 6′-or 2′, 6′-dihydroxylation of the B ring and a 5, 7-dihydroxylation of the A ring results in significant activity against methicillin-resistant *Staphylococcus aureus* (MRSA). Substitution with a certain aliphatic group at the 6- or 8- position also enhances the anti-MRSA activity. Among the differently substituted flavanones isolated from *Sophora exigua* (Leguminosae) and *Echinosophora koreensis* (Leguminosae) which possessed these structural characteristics, 5,7 ,2′,6′-tetrahydroxy-6-isoprenyl-8 - lavandulyl-4′-methoxy-flavanone (exiguaflavanone D) and 5,,2′,6′-trihydroxy-6-isoprenyl-8-lavandulyl-7-methoxy-flavanone (exiguaflavanone B) had a minimum inhibitory concentration of 1.56–6.25 µg/ml and 50 µg/ml, respectively, for all MRSA strains examined.

Two new isoflavans and the known constituent 2′,7-hydroxy-3′,4′,8-trimethoxyisoflavan (isoduratin) have been isolated from the bark and trunk of *Eysenhardtia polystachya* (Leguminosae). Spectroscopic analysis identified the unknown isoflavans as (3S)-7-hydroxy-2′,3′,4′,8-pentamethoxyisoflavan and (3S)-3′,7-hydroxy-2′,4′,5′,8-tetramethoxyisoflavan. These new compounds along with the isoduratin demonstrated moderate cytotoxic activity against certain cell lines.

The prior art is deficient in any description of biologically active flavanones from desert legumes that are of potential biomedical significance. The present invention fulfills this long-standing need and desire in the art.

SUMMARY OF THE INVENTION

Figure 1:
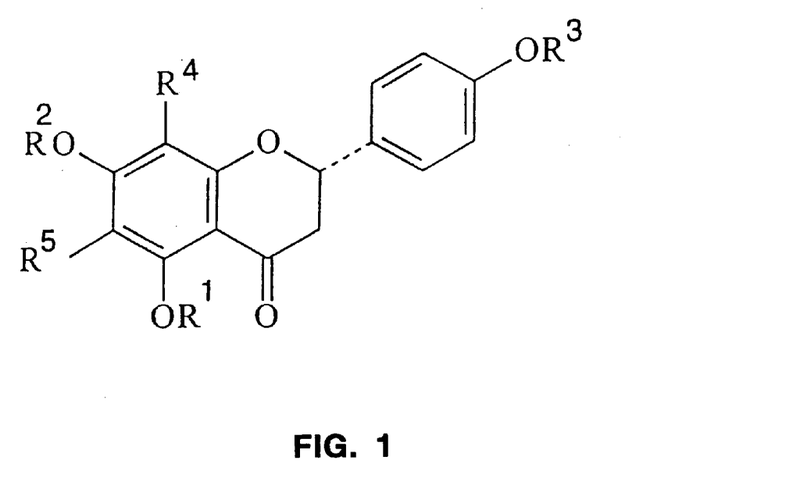
FIG. 1 shows the general chemical structure of flavanones.

In one embodiment of the present invention, there is provided a flavanone compound isolated from *Eysenhardtia texana* having the structural formula:

wherein R′ is selected from the group consisting of hydrogen, a C1–C25 alkyl group, a C1–C25 alkenyl group, a C1–C25 alkynyl group, aryl, aryl halide, alkyl carbonyl and aryl carbonyl; $R^2$ is selected from the group consisting of hydrogen, a C1–C25 alkyl group, a C1–C25 alkenyl group, a C1–C25 alkynyl group, aryl, aryl halide, alkyl carbonyl and aryl carbonyl; $R^3$ is selected from the group consisting of hydrogen, a C1–C25 alkyl group, a C1–C25 alkenyl group, a C1–C25 alkynyl group, aryl, aryl halide, alkyl carbonyl and aryl carbonyl; $R^4$ is selected from the group consisting of hydrogen, a C1–C25 alkyl group, a C1–C25 alkenyl group, a C1–C25 alkynyl group, aryl, aryl halide, alkyl carbonyl and aryl carbonyl; and $R^5$ is selected from the group consisting of hydrogen, a C1–C25 alkyl group, a C1–C25 alkenyl group, a C1–C25 alkynyl group, aryl, aryl halide, alkyl carbonyl and aryl carbonyl.

Figure 2:
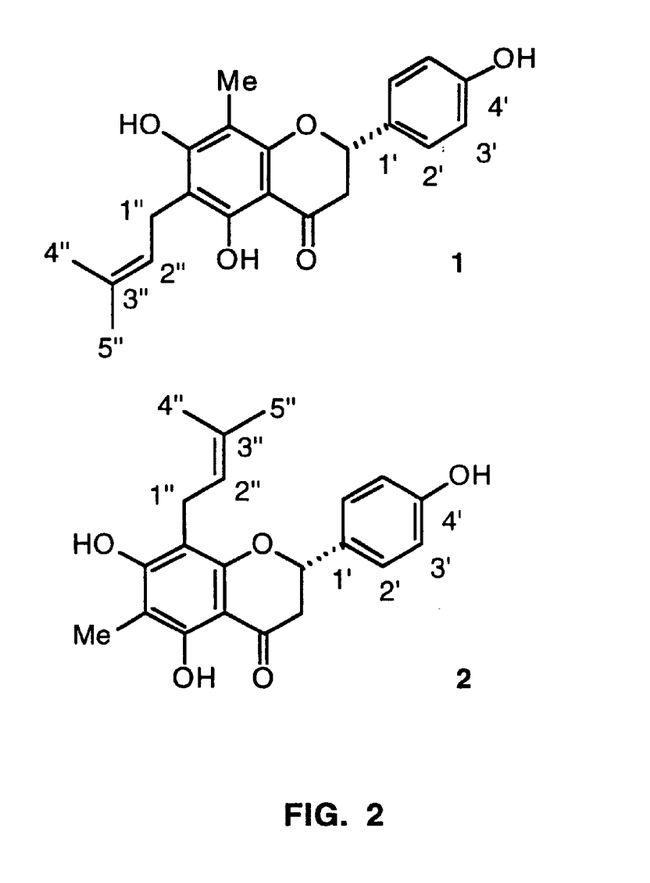
FIG. 2 shows the general chemical structure of 4',5,7-trihydroxy-8-methyl-6-(3-methyl-[2-butenyl])-(2S)-flavanone (1) and 4',5,7-trihydroxy-6-methyl-8-(3-methyl-[2-butenyl])-(2S)-flavanone (2).

In another embodiment of the present invention there is provided a compound having the structural formula:

In yet another embodiment of the present invention there is provided a compound having the structural formula:

2

In yet another embodiment of the present invention, there is provided a pharmaceutical composition comprising a compound disclosed herein and a pharmaceutically acceptable carrier.

In yet another embodiment of the present invention, there is provided a method of killing bacteria or fungi in an individual in need of such treatment, comprising the step of administering a pharmacologically effective dose of the pharmaceutical composition disclosed herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

When plants from arid regions were screened for possible biomedical uses, the antifungal and antibacterial properties of the methanol-dichloromethane extract obtained from *Eysenhardtia texana* Kunth. (Fabaceae) were observed. *Eysenhardtia texana* is an irregularly shaped shrub, which is also regionally known as "Texas kidneywood". *Eysenhardtia texana* grows on the high calcareous soils of South Texas (north to Bell, San Saba, Crockett and Brewster counties) south to the Mexican states of Coahuila and Tamaulipas. It is usually 2–3 meters tall, the leaves are 3–9 cm long with 15–47, mostly 5–15 mm long leaflets (1, 2).

Bioactivity-guided fractionation using a gel-diffusion assay (3) for monitoring of the antimicrobial and antifungal activity has led to the isolation of prenylated flavanones from *E. texana*. The structural elucidation of two of these new antibacterial and antifungal flavanones is determined by means of techniques including UV absorbance spectra, nuclear magnetic resonance (NMR) spectra and electrospray ionization mass spectroscopy (ESIMS). Bioassay data for the novel flavanones' fungicidal and bactericidal properties is also provided.

It is specifically contemplated that pharmaceutical compositions may be prepared using the novel flavanones of the present invention. In such a case, the pharmaceutical composition comprises the novel flavanones of the present invention and a pharmaceutically acceptable carrier. A person having ordinary skill in this art would readily be able to determine, without undue experimentation, the appropriate dosages and routes of administration of this flavanone of the present invention.

When used in vivo for therapy, the flavanone of the present invention is administered to the patient or an animal in therapeutically effective amounts, i.e., amounts that eliminate or reduce the bacterial or fungal burden. It will normally be administered parenterally, preferably intravenously, but other routes of administration will be used as appropriate. The dose and dosage regimen will depend upon the nature of the bacterial or fungal infection and the patient, the patient's history and other factors. The amount of flavanone administered will typically be in the range of about 0.01 mg/kg to about 100 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed. (1990) Pergamon Press. For parenteral administration, the flavanone will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives.

Thus the present invention is directed toward the isolation and identification of novel flavanones. Preferably, these compounds are isolated from a desert legume, *Eysenhardtia texana* and possess a biochemical action selected from the group consisting of antifungal and antimicrobial properties. More specifically, the present invention isolates, identifies and characterizes the antifungal and antimicrobial activities of the novel flavanones 4',5,7-trihydroxy-8-methyl-6-(3-methyl-[2-butenyl])-(2S)-flavanone and 4',5,7-trihydroxy-6-methyl-8-(3-methyl-[2-butenyl])-(2S)-flavanone.

The following examples are given for the purpose of illustrating various embodiments of the invention and are not meant to limit the present invention in any fashion:

EXAMPLE 1

Material and Methods $^1$H and $^{13}$C NMR spectra were recorded in $CDCl_3$ with TMS as internal standard on a Varian Unity at 300 and 75.4 MHz, respectively. EIMS were recorded on a Hewlett Packard 5988A at 200° C., 70 eV. APCIMS were recorded with a Finnegan TSQ 7000. HREIMS were recorded on a JEOL HX 110 spectrometer with a resolution of 10,000. Optical rotation was determined on a Autopol III polarimeter. A Hitachi HPLC system equipped with a L4500 diode array detector was used for the final purification step. Shifts of UV maxima were measured on a Bausch & Lomb Spectronic 21 spectrophotometer following described procedures (6).

EXAMPLE 2

Determination of biological activity

The agar diffusion assay was carried out as described in the literature (3) the only modifications being the use of DMSO (total concentration 5%) and SD agar. *S. aureus* and *C. albicans* from the collection maintained at the Bioresources Research Facility were used.

At a concentration of 0.1 mg/ml compound 1 and compound 2 inhibited growth of *Staphylococcus aureus*, and compound 1 also inhibited the growth of *Candida albicans* in an agar-gel diffusion assay. Antibacterial and antifungal activity at this concentration is typical for a variety of prenylated flavonoids described by others (7).

EXAMPLE 3

Plant material

Aerial parts of *E. texana* were obtained from the Desert Legume Program (DELEP), College of Agriculture, The University of Arizona. A voucher specimen collected Jul. 12, 1990 in Val Verde County, Tex., was deposited in the Herbarium of The University of Arizona as ARIZ291230.

EXAMPLE 4

Extraction and isolation

The EtOAc soluble part of 10.9 g $CH_2CL_2$-MeOH extract obtained from 150 g dried plant material (aerial parts) was chromatographed with hexane-EtOAc and EtOAc-propan-2-ol mixtures on 600 g silica gel. The resulting fractions were assayed for growth inhibitory activity against *S. aureus* and *C. albicans*. Column chromatography of the most active fraction with Sephadex LH20 and silica gel, prep. TLC, and HPLC on RP18 gave 2.8 mg of compound 1, 1.5 mg of compound 2, and 0.6 mg of compound 3.

EXAMPLE 5

UV and NMR spectra (6)

Maxima of UV absorbance around 290 nm and AMX spin systems in the aliphatic region of the $^1H$ NMR spectra suggested flavanone structures for compounds 1 and compound 2. The HRMS of compound 1 and compound 2 were in accordance with molecular formulas $C_{21}H_{22}O_5$ (requires: 354.1467, found: 354.1477 and 354.1459). Bathochromic shifts upon addition of $AlCl_3$ and $AlCl_3$/HCl, and $^1H$ NMR resonances for chelated hydroxy protons at $d_H$ 12.4, 12.3, and 12.1 indicated 5-hydroxy substitution. In the aromatic region of the $^1H$ NMR spectra the compounds showed AA'BB' spin systems at almost identical positions typical for a 4'-monosubstituted B ring. Molecular ion peaks at m/z 354 for compound 1 and compound 2 with A ring fragments at m/z 234 and B ring fragments at m/z 120 indicated a 4'-hydroxylated B ring for the compounds. They also showed $^1H$ NMR signals indicative of methyl substituents at an aromatic ring.

Additionally, compound 1 and compound 2 gave bathochromic shifts upon addition of sodium acetate indicating 7-hydroxy substitution. The presence of dimethylallyl groups was evidenced by the two singlets for two methyl groups, a doublet for a methylene group, and a multiplet for the vinylic proton all at positions typical for dimethylallyl groups attached to aromatic rings.

TABLE 1

$^{13}C$ and $^1H$ NMR data of compounds 1 and 2 in $CDCl_3$

| C/H | compound 1 $^{13}C$ | compound 1 $^1H$ | compound 2 $^{13}C$ | compound 2 $^1H$ |
|---|---|---|---|---|
| 2 | 78.3 d | 5.35 dd (3.0, 12.7) | 78.6 d | 5.32 dd (3.0, 12.9) |
| 3 ax | 43.3 t | 3.04 dd (17.1, 12.7) | 43.3 t | 3.05 dd (17.1, 12.9) |
| 3 eq. | " | 2.81 dd (17.1, 3.0) | " | 2.80 dd (17.1, 3.3) |
| 4 | 196.5 s | — | 196.5 s | — |
| 4a | 102.8 s | — | 102.7 s | — |
| 5 | 158.8 s | — | 159.8 s | — |
| 6 | 106.0 s | — | 105.1 s | — |
| 7 | 162.2 s | — | 162.0 s | — |
| 8 | 103.3 s | — | 104.4 s | — |
| 8a | 158.2 s | — | 157.2 s | — |
| 1' | 131.2 s | — | 131.0 s | — |
| 2'/6' | 127.7 d | 7.34 AA'BB' (8.4) | 127.7 d | 7.33 AA'BB' (8.4) |
| 4' | 155.9 s | — | 155.9 s | — |
| 3'/5' | 115.6 d | 6.89 AA'BB' (8.4) | 115.5 d | 6.88 AA'BB' (8.4) |
| 5-OH | — | 12.4 s | — | 12.3 s |
| 8- or 6-Me | 7.5 q | 2.01 s | 6.9 q | 2.04 s |
| 1" | 21.3 t | 3.39 br d (7.0) | 22.0 t | 3.35 br d (7.2) |
| 2" | 121.6 d | 5.25 br t (7.0) | 121.7 d | 5.25 br t (7.2) |
| 3" | 136.1 s | — | 135.7 s | — |
| 4" | 17.8 q | 1.84 s | 17.8 q | 1.77 s* |
| 5" | 25.9 q | 1.78 s | 25.9 q | 1.75 s* |

*values in column interchangeable

EXAMPLE 6

HMBC and DEPT elucidation of chemical structure

These standard nuclear magnetic resonance (NMR) methods were performed using standard software provided by the manufacturer of the NMR instrument, a Unity 300 spectrometer by Varian.

The positions of the prenyl and methyl groups in compounds 1 and 2 were determined by HMBC experiments. The chelated 5-hydroxy proton of compound 1 at $d_H$ 12.4 showed crosspeaks with carbons at $d_C$ 158.8, 106.0, and 102.8 and the prenyl methylene protons at $d_H$ 3.39 showed crosspeaks at $d_C$ 158.8, 162.2, 136.1, 121.6, and 106.0. Consequently, the position of the prenyl group in compounds is at 6. The $^1H$ and $^{13}C$ NMR spectra, DEPT and HMBC experiments together with published data for naringenin [6] also allowed the assignment of carbon and proton shifts for compounds 1 and 2 (Table 1). The proton signal of the methyl group at the A-ring of compound 2 gave rise to crosspeaks with carbons at $d_C$ 162.0, 159.8, and 105.1 from which its 6-position follows. The levorotatory nature of compounds 1 and 2 indicated normal S stereochemistry at C-2. Therefore, compounds 1 and 2 were assigned the structures of 4',5,7-trihydroxy-8-methyl-6-(3-methyl-[2-butenyl])-(2S)-flavanone and 4',5,7-trihydroxy-6-methyl-8-(3-methyl-[2-butenyl])flavanone, respectively.

EXAMPLE 7

Compound characteristics

4',5,7-trihydroxy-8-methyl-6-(3-methyl-[2-butenyl])-(2S)-flavanone (1) UV $\lambda_{max}$ (nm) MeOH: 296, $AlCl_3$: 320, $AlCl_3$/HCl: 318, NaOAc: 342, NaOAc/$H_3BO_3$: 296. $[\alpha]_D$ −5.9° (MeOH, c 0.24). EIMS m/z (rel. int.): 354 (46), 339 (10), 311 (10), 299 (20), 234 (24), 219 (52), 206 (44), 191 (36), 179 (100), 120 (38). APCIMS: m/z 355.

4',5,7-trihydroxy-8-methyl-6-(3-methyl-[2-butenyl])-(2S)-flavanone (2) UV $\lambda_{max}$ (nm): MeOH: 296, $AlCl_3$: 320, $AlCl_3$/HCl: 318, NaOAc: 336, NaOAc/$H_3BO_3$: 296. $[\alpha]_D$ −14.7° (MeOH, c 0.14). EIMS m/z (rel. int.): 354 (56), 339

(15), 311(13), 299 (23), 234 (27), 219 (66), 206 (47), 191 (76), 179 (100), 120 (39). APCIMS: m/z 355.

Thus, the present invention is directed to a compound having the structural formula:

wherein $R^1$ is selected from the group consisting of hydrogen, a C1–C25 alkyl group, a C1–C25 alkenyl group, a C1–C25 alkynyl group, aryl, aryl halide, alkyl carbonyl and aryl carbonyl; $R^2$ is selected from the group consisting of hydrogen, a C1–C25 alkyl group, a C1–C25 alkenyl group, a C1–C25 alkynyl group, aryl, aryl halide, alkyl carbonyl and aryl carbonyl; $R^3$ is selected from the group consisting of hydrogen, a C1–C25 alkyl group, a C1–C25 alkenyl group, a C1–C25 alkynyl group, aryl, aryl halide, alkyl carbonyl and aryl carbonyl; $R^4$ is selected from the group consisting of hydrogen, a C1–C25 alkyl group, a C1–C25 alkenyl group, a C1–C25 alkynyl group, aryl, aryl halide, alkyl carbonyl and aryl carbonyl; and $R^5$ is selected from the group consisting of hydrogen, a C1–C25 alkyl group, a C1–C25 alkenyl group, a C1–C25 alkynyl group, aryl, aryl halide, alkyl carbonyl and aryl carbonyl. In one aspect, the compound has the structure:

In a different embodiment, the compound has the structural formula:

Preferably, the compound is isolated from a desert legume, *Eysenhardtia texana*. Such compounds have a biochemical action selected from the group consisting of antifungal and antimicrobial properties.

The compounds of the present invention may be administered alone or in a pharmaceutical composition, e.g., the compound and a pharmaceutically acceptable carrier.

The present invention is directed to a method of killing bacteria or fungi in an individual in need of such treatment, comprising the step of administering a pharmacologically effective dose of the pharmaceutical composition of claim 1 to said individual. Furthermore, the present invention is directed to a method of killing bacteria or fungi, comprising the step of contacting said bacteria or fungi with a pharmacologically effective dose of the compound disclosed herein.

The following references were cited herein:
1. Corell, D. S., Johhnston, M. C. *Manual of the Vascular Plants of Texas,* Texas Research Foundation, Renner, 1970, p 819.
2. Vines, R. A. *Trees, Shrubs, and Woody Vines of the Southwest,* University of Texas Press, Austin, 1960, p 528.
3. Mitscher, L. A., Leu, R.-P., Bathala, M. S., Wu, W.-N., Beal, J. L. and White R. *Lloydia,* 1972, 35, 157.
4. Mahmoud, E. N. and Waterman, P. G. *J. Nat. Prod.,* 1985, 48, 648.
5. Horowitz, R. M. and Gentili B. *Chem. and Ind.,* 1964, 498.
6. Markham, K. R. *Techniques of Flavonoid Identification,* Academic Press, London, 1982, pp 36–51 and 84.
7. Goodwin, T. W. and Mercer, E. I. *Introduction to Plant Biochemistry,* Pergamon Press, Oxford, 1983, pp. 541–545.
8. Mitscher, L. A., Drake, S., Gollapudi, S. R., and Okwute, S. K. *J. Nat. Prod.,* 1987, 50, 1025.
9. Tsuchiya H., Sato, M., Miyazaki, T. Fujiwara, S., Ohyama, M. Tanaka, T., and Iinuma, M. *J. of Ethnopharmacology,* 1996, 50, 27–34.
10. Iinuma, M., Tsuchiya H., Sato, Yokoyama, J., M., Ohyama, M., Ohkawa, Y., Tanaka, T., Fujiwara, S., and Fujii, T. J. of Pharmacy & Pharmacology, 1994, 46, 892–895.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:
1. A substantially pure compound having a structural formula:

wherein $R^1$ is hydrogen;
$R^2$ and $R^3$ are selected from the group consisting of hydrogen and methyl; and
$R^4$ and $R^5$ are selected from the group consisting of methyl and a C5 alkenyl group;

wherein when $R^4$ is methyl, $R^5$ is not methyl:

wherein when $R^4$ is an isopentenyl group, $R^5$ is not an isopentenyl group.

2. The compound of claim 1 having the structure:

3. The compound of claim 2, wherein said compound is 4',5,7-trihydroxy-8-methyl-6-(3-methyl-[2-butenyl])-(2S)-flavanone.

4. The compound of claim 1 having a structural formula:

5. The compound of claim 4, wherein said compound is 4',5,7-trihydroxy-6-methyl-8-(3-methyl-[2-butenyl])-(2S)-flavanone.

6. The compound of claim 1, wherein said compound is isolated from a desert legume, *Eysenhardtia texana*.

7. The compound of claim 1, wherein said compound has a biochemical action selected from the group consisting of antifungal, antimicrobial and antifungal/antimicrobial properties.

8. A pharmaceutical composition, comprising the compound of claim 1 and a pharmaceutically acceptable carrier.

9. A method of killing bacteria or fungi in an individual in need of such treatment, comprising the step of administering a pharmacologically effective dose of the pharmaceutical composition of claim 8 to said individual.

10. A method of killing bacteria or fungi, comprising the step of contacting said bacteria or fungi with a pharmacologically effective dose of the compound of claim 1.

11. A method of killing bacteria or fungi, comprising the step of contacting said bacteria or fungi with a pharmacologically effective dose of the compound of claim 2.

12. A method of killing bacteria or fungi, comprising the step of contacting said bacteria or fungi with a pharmacologically effective dose of the compound of claim 4.

13. The compound of claim 2, wherein said compound has a biochemical action comprising antimicrobial properties.

* * * * *

UNITED STATES PATENT AND TRADEMARK OFFICE
CERTIFICATE OF CORRECTION

PATENT NO.   : 6,136,849
DATED        : Oct 24, 2000
INVENTOR(S)  : Joseph J. Hoffman, et al.

It is certified that error appears in the above-identified patent and that said Letters Patent is hereby corrected as shown below:

Column 1:
Line 10, the caption "BACKGROUND OF THE INVENTION" should be above the caption "CROSS REFERENCE TO RELATED APPLCATIONS" in line 4.

Column 1:
In the structural formula, line 25, "B" should be in bold
In the structural formula, line 27, "A" should be in bold.
Line 60, "5,7 ,2'6" should read --5,7,2'6--.
Line 60 "isoprenyl-8 -lavandulyl" should read --isoprenyl-8-lavandulyly--.
Line 62, "5,,2" should read --5,2--.

Column 2:
In the second structural formula, line57, please replace the hash marks linking the two ring structures with a dashed line linking the two ring structures as in the first structural formula.

UNITED STATES PATENT AND TRADEMARK OFFICE
CERTIFICATE OF CORRECTION

PATENT NO. : 6,136,849
DATED : Oct 24, 2000
INVENTOR(S) : Joseph J. Hoffman, et al.

It is certified that error appears in the above-identified patent and that said Letters Patent is hereby corrected as shown below:

Column 3:
In the structural formula, line 8, please replace the hash marks linking the two ring structures with a dashed line linking the two ring structures as in the structural formulas in Column 2.

Column 4:
Lines 27-28, "See Remington's Pharmaceutical Science" should be italicized.

Column 5: line 8, please insert a comma between the words "(3)" and "the only".
Line 8, please insert the word --that-- between the words "being" and "the use".
Line 50, "$d_H$" should not be italicized.
Line 55, "$m/z$" should be italicized.
Line 57, "$m/z$" should be italicized.

Column 6:
Line 38, "$d_H$" should not be italicized.
Line 39, "$d_C$" should not be italicized.
Line 40, "$d_H$" should not be italicized.
Line 41, "$d_C$" should not be italicized.

UNITED STATES PATENT AND TRADEMARK OFFICE
CERTIFICATE OF CORRECTION

PATENT NO.   : 6,136,849
DATED        : Oct 24, 2000
INVENTOR(S)  : Joseph J. Hoffman, et al.

It is certified that error appears in the above-identified patent and that said Letters Patent is hereby corrected as shown below:

Column 6:
Line 48, "$d_C$" should not be italicized.
Lines 58-59, "trihydroxy-8-methyl-6-(3-methyl-[2-butenyl])-(2S)-flavanone" should read --*trihydroxy-8-methyl-6-(3-methyl-[2-butenyl])-(2S)-flavanone*--.

Line 59, "$\lambda max$" should not be italicized.
Line 63, "m/z" should be italicized.
Lines 64-65, "trihydroxy-8-methyl-6-(3-methyl-[2-butenyl])-(2)-flavanone" should read –*trihydroxy-8-methyl-6-(3-methyl-[2-butenyl])-(2S)-flavanone*--.

Line 65, "$\lambda max$" should not be italicized.
Line 66, "$[\alpha]_D$ should not be italicized.
Line 67, "m/z" should be italicized.

Column 7:
Line 2, "m/z" should be italicized.
In the second structural formula, line 36, please replace the hash marks linking the two ring structures with a dashed line linking the two ring structures as in the first structural formula.

UNITED STATES PATENT AND TRADEMARK OFFICE
CERTIFICATE OF CORRECTION

PATENT NO. : 6,136,849
DATED : Oct 24, 2000
INVENTOR(S) : Joseph J. Hoffman, et al.

It is certified that error appears in the above-identified patent and that said Letters Patent is hereby corrected as shown below:

Column 7:
In the third structural formula, line 55, please replace the hash marks linking the two ring structures with a dashed line linking the two ring structures as in the first and second structural formulas.

Column 8:
Line 15, please insert --pp-- between the words "1985," and "48,".
Line 17, please insert --p-- between the words "1964," and "498."
Line 24, please insert --pp-- between the words "1987," and "50,".
Line 27, please insert --pp-- between the words "1994," and "46,".

Signed and Sealed this

Twelfth Day of June, 2001

*Attest:*

NICHOLAS P. GODICI
*Attesting Officer*    Acting Director of the United States Patent and Trademark Office

UNITED STATES PATENT AND TRADEMARK OFFICE
CERTIFICATE OF CORRECTION

PATENT NO.  : 6,136,849
DATED       : Oct 24, 2000
INVENTOR(S) : Joseph J. Hoffman, et al.

It is certified that error appears in the above-identified patent and that said Letters Patent is hereby corrected as shown below:

Column 1:
Line 10, the caption "BACKGROUND OF THE INVENTION" should be above the caption "CROSS REFERENCE TO RELATED APPLCATIONS" in line 4.
Line 60, "5,7 ,2'6" should read --5,7,2'6--.
Line 60 "isoprenyl-8 -lavandulyl" should read --isoprenyl-8-lavandulyly--.
Line 62, "5,,2" should read --5,2--.Line 60, "5,7 ,2'6" should read --5,7,2'6--.
Line 60 "isoprenyl-8 -lavandulyl" should read --isoprenyl-8-lavandulyly--.
Line 62, "5,,2" should read --5,2--.

Column 1: Structural formula,
Line 25, "B" should be in bold
Line 27, "A" should be in bold.

Column 2:
In the second structural formula, line 57, please replace the hash marks linking the two ring structures with a dashed line linking the two ring structures as in the first structural formula.

UNITED STATES PATENT AND TRADEMARK OFFICE
CERTIFICATE OF CORRECTION

PATENT NO. : 6,136,849
DATED : Oct 24, 2000
INVENTOR(S) : Joseph J. Hoffman, et al.

It is certified that error appears in the above-identified patent and that said Letters Patent is hereby corrected as shown below:

Column 3: Structural formula,
Line 8, please replace the hash marks linking the two ring structures with a dashed line linking the two ring structures as in the structural formulas in Column 2.

Column 4:
Lines 27-28, "See Remington's Pharmaceutical Science" should be italicized.

Column 5:
Line 8, please insert a comma between the words "(3)" and "the only".
Line 8, please insert the word --that-- between the words "being" and "the use".
Line 50, "$d_H$" should not be italicized.
Line 55, "m/z" should be italicized.
Line 57, "m/z" should be italicized.

Column 6:
Line 38, "$d_H$" should not be italicized.
Line 39, "$d_C$" should not be italicized.
Line 40, "$d_H$" should not be italicized.
Line 41, "$d_C$" should not be italicized.

UNITED STATES PATENT AND TRADEMARK OFFICE
CERTIFICATE OF CORRECTION

PATENT NO. : 6,136,849
DATED : Oct 24, 2000
INVENTOR(S) : Joseph J. Hoffman, et al.

It is certified that error appears in the above-identified patent and that said Letters Patent is hereby corrected as shown below:

Column 6:
Line 48, "$d_C$" should not be italicized.
Lines 58-59, "trihydroxy-8-methyl-6-(3-methyl-[2-butenyl])-(2S)-flavanone" should read --*trihydroxy-8-methyl-6-(3-methyl-[2-butenyl])-(2S)-flavanone*--.

Line 59, "$\lambda max$" should not be italicized.
Line 63, "m/z" should be italicized.
Lines 64-65, "trihydroxy-8-methyl-6-(3-methyl-[2-butenyl])-(2)-flavanone" should read --*trihydroxy-8-methyl-6-(3-methyl-[2-butenyl])-(2S)-flavanone*--.

Line 65, "$\lambda max$" should not be italicized.
Line 66, "$[\alpha]_D$ should not be italicized.
Line 67, "m/z" should be italicized.

Column 7:
Line 2, "m/z" should be italicized.
In the second structural formula, line 36, please replace the hash marks linking the two ring structures with a dashed line linking the two ring structures as in the first structural formula.

UNITED STATES PATENT AND TRADEMARK OFFICE
CERTIFICATE OF CORRECTION

PATENT NO. : 6,136,849
DATED : Oct 24, 2000
INVENTOR(S) : Joseph J. Hoffman, et al.

It is certified that error appears in the above-identified patent and that said Letters Patent is hereby corrected as shown below:

Column 7:
In the third structural formula, line 55, please replace the hash marks linking the two ring structures with a dashed line linking the two ring structures as in the first and second structural formulas.

Column 8:
Line 15, please insert --pp-- between the words "1985," and "48,".
Line 17, please insert --p-- between the words "1964," and "498."
Line 24, please insert --pp-- between the words "1987," and "50,".
Line 27, please insert --pp-- between the words "1994," and "46,".

Signed and Sealed this

Twenty-sixth Day of June, 2001

*Attest:*

*Attesting Officer*

NICHOLAS P. GODICI
*Acting Director of the United States Patent and Trademark Office*